United States Patent
Yen et al.

(10) Patent No.: US 10,384,996 B2
(45) Date of Patent: Aug. 20, 2019

(54) FLUORENE-CONTAINING COMPOUND AND METHOD FOR MAKING THE SAME

(71) Applicant: NATIONAL KAOHSIUNG UNIVERSITY OF APPLIED SCIENCES, Kaohsiung (TW)

(72) Inventors: Fu-San Yen, Kaohsiung (TW); Chi-Han Hsieh, Kaohsiung (TW)

(73) Assignee: National Kaohsiung University of Applied Sciences, Kaohsiung (TW)

(*) Notice: Subject to any disclaimer, the term of this patent is extended or adjusted under 35 U.S.C. 154(b) by 0 days.

(21) Appl. No.: 15/650,992

(22) Filed: Jul. 17, 2017

(65) Prior Publication Data
US 2018/0208531 A1 Jul. 26, 2018

(30) Foreign Application Priority Data
Jan. 25, 2017 (TW) .............................. 106102883 A

(51) Int. Cl.
| | |
|---|---|
| C07C 37/84 | (2006.01) |
| C07C 37/11 | (2006.01) |
| C08G 61/12 | (2006.01) |
| C07C 69/54 | (2006.01) |
| C07C 39/17 | (2006.01) |
| C07C 43/215 | (2006.01) |
| C07C 43/23 | (2006.01) |
| C07C 271/16 | (2006.01) |
| C07C 271/48 | (2006.01) |
| C07D 303/23 | (2006.01) |

(52) U.S. Cl.
CPC ............ *C07C 37/115* (2013.01); *C07C 37/84* (2013.01); *C07C 39/17* (2013.01); *C07C 43/215* (2013.01); *C07C 43/23* (2013.01); *C07C 69/54* (2013.01); *C07C 271/16* (2013.01); *C07C 271/48* (2013.01); *C07D 303/23* (2013.01); *C08G 61/12* (2013.01); *C07C 2603/18* (2017.05)

(58) Field of Classification Search
CPC combination set(s) only.
See application file for complete search history.

(56) References Cited

U.S. PATENT DOCUMENTS 4,675,458 A * 6/1987 Riemann ................. C07C 37/20
568/719

FOREIGN PATENT DOCUMENTS

WO WO 2015141710 * 9/2015

OTHER PUBLICATIONS

Machine translation available for WO 2015141710.*

* cited by examiner

*Primary Examiner* — Ana Z Muresan
(74) *Attorney, Agent, or Firm* — Marshall & Melhorn, LLC

(57) ABSTRACT

A fluorene-containing compound having a formula (I)

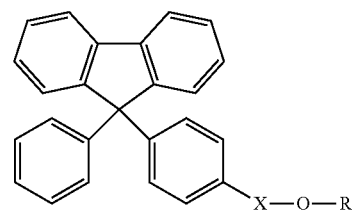

where X and R are as defined in as defined in the specification.

6 Claims, No Drawings

FLUORENE-CONTAINING COMPOUND AND METHOD FOR MAKING THE SAME

CROSS-REFERENCE TO RELATED APPLICATION

This application claims priority from Taiwanese patent application no. 106102883, filed on Jan. 25, 2017.

FIELD

The disclosure relates to a fluorene-containing compound, more particularly to a fluorene-containing compound and a method for making the same.

BACKGROUND

U.S. Pat. No. 4,675,458 discloses a method for making 9,9-bis-(4-hydroxyphenyl)-fluorene, which is useful in making various types of fluorene-containing compounds. The fluorene-containing compounds are widely used in the fields of pharmaceuticals as disclosed in WO2012145330A1, optics as disclosed in US 2013/0266763 A1, flame-retardant research as disclosed in US20140179836 A1, etc. Many of such fluorene-containing compounds are prepared from 9,9-bis-(4-hydroxyphenyl)-fluorene or its derivatives, and thus, they normally have two phenyl groups each having a substituted group.

Biphenyl-phenyl-4'-yl-phenyl-methanol is disclosed in F. Ullmann and R. von Wurstemberger, "Veber Derivate des Biphenylendiphenylmethans," Chemische Berichte, vol. 37, 1904, pages 73-78.

Condensation of carbinol with phenol is disclosed in A. Kliegl, "Ueber die Condensation von Benzaldehyd mit Toluol," Chemische Berichte, vol. 38, 1905, pages 84-87.

SUMMARY

Therefore, an object of the disclosure is to provide a novel fluorene-containing compound and a method for making the same. The novel fluorene-containing compound has a refractive index not less than 1.54.

According to a first aspect of the disclosure, a fluorene-containing compound having a formula (I)

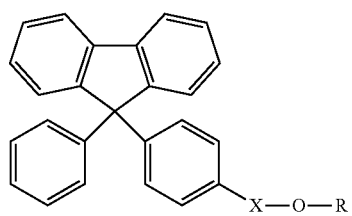

where:
X is a single bond or $-(\text{O}-\text{X}^1-)_n$ in which n ranges from 1 to 3 and $X^1$ is

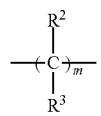

in which m ranges from 1 to 4, and each of $R^2$ and $R^3$ is the same or different in each repeating unit m, and is independently a hydrogen atom, an alkyl group, an alkenyl group, or a hydroxyl group; and R is selected from the group consisting of a hydrogen atom, an epoxy-containing group, an alkenyl group, an unsaturated acyl group, an alkyl-substituted unsaturated acyl group,

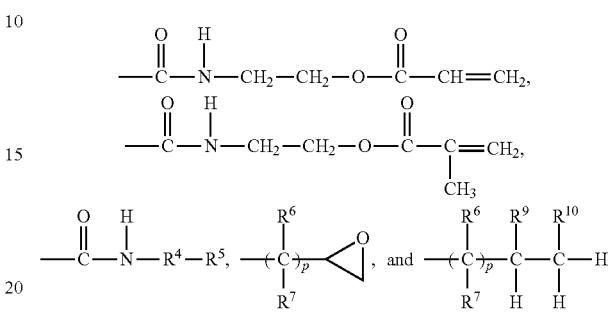

in which
$R^4$ is an alkylene group,
$R^5$ is an acrylate group or a methacrylate group,
p ranges from 1 to 4,
each of $R^6$ and $R^7$ is the same or different in each repeating unit p, and is independently a hydrogen atom, an alkyl group, or a hydroxyl group, and
one of $R^9$ and $R^{10}$ is a hydroxyl group and the other of $R^9$ and $R^{10}$ is

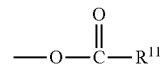

in which $R^{11}$ is an unsubstituted alkenyl group or an alkyl-substituted alkenyl group,
with the proviso that when X is a single bond, R is not a hydrogen atom.

According to a second aspect of the disclosure, a method for making a fluorene-containing compound includes the steps of:
(a) providing a precursor compound having a formula

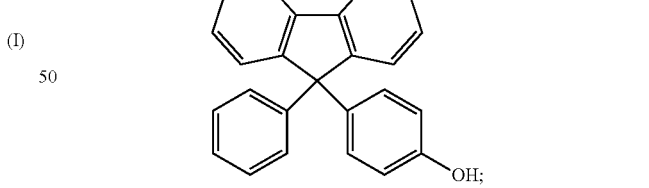

(b) providing a first organic compound selected from the group consisting of alkenyl halide, alkylene oxide, an epoxy-containing unsaturated compound, an epoxy-containing alkyl halide, an unsaturated acyl halide, an alkyl-substituted unsaturated acyl halide, an unsaturated carboxylic acid, an alkyl-substituted unsaturated carboxylic acid, halohydrin,

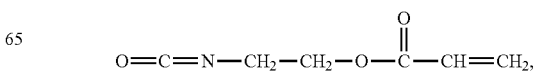

-continued

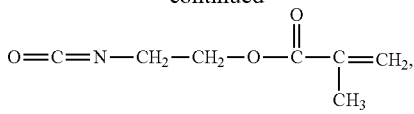

$O=C=N-R^4-R^5$, in which $R^4$ is an alkylene group and $R^5$ is an acrylate group or a methacrylate group, and combinations thereof; and (c) reacting the precursor compound with the first organic compound in a first solvent to obtain a fluorene-containing compound of formula (III)

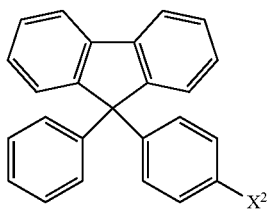 (III)

where $X^2$ is $-(O-X^1-)_n OH$, or $-O-R^1$, in which n ranges from 1 to 3,
$X^1$ is

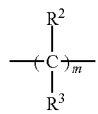

in which m ranges from 1 to 4, and each of $R^2$ and $R^3$ is the same or different in each repeating unit m, and is independently a hydrogen atom, an alkyl group, an alkenyl group, or a hydroxyl group, and $R^1$ is selected from the group consisting of an alkenyl group, an epoxy-containing group, an unsaturated acyl group, an alkyl-substituted unsaturated acyl group,

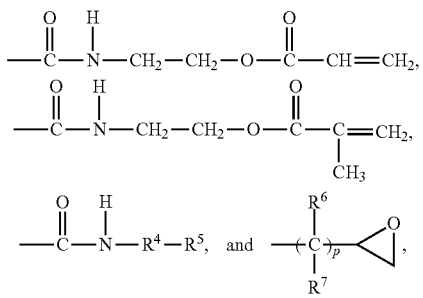

in which p ranges from 1 to 4, and each of $R^6$ and $R^7$ is the same or different in each repeating unit p, and is independently a hydrogen atom, an alkyl group, or a hydroxyl group.

According to a third aspect of the disclosure, a curable composition includes the fluorene-containing compound.

According to a fourth aspect of the disclosure, a polymer composition includes the curable composition.

DETAILED DESCRIPTION

A fluorene-containing compound according to an embodiment of the disclosure has a formula (I)

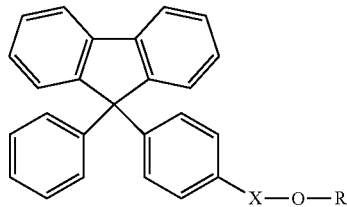 (I)

where:
X is a single bond or $-(O-X^1-)_n$ in which n ranges from 1 to 3 and $X^1$ is

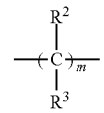

in which m ranges from 1 to 4, and each of $R^2$ and $R^3$ is the same or different in each repeating unit m, and is independently a hydrogen atom, an alkyl group, an alkenyl group, or a hydroxyl group; and R is selected from the group consisting of a hydrogen atom, an epoxy-containing group, an alkenyl group, an unsaturated acyl group, an alkyl-substituted unsaturated acyl group,

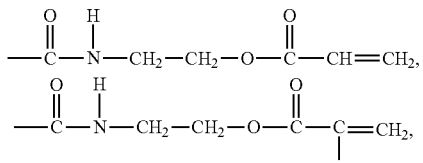

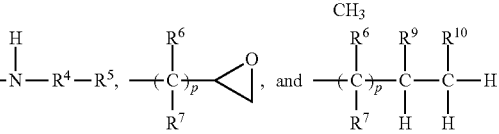

in which
$R^4$ is an alkylene group,
$R^5$ is an acrylate group or a methacrylate group,
p ranges from 1 to 4,
each of $R^6$ and $R^7$ is the same or different in each repeating unit p, and is independently a hydrogen atom, an alkyl group, or a hydroxyl group, and
one of $R^9$ and $R^{10}$ is a hydroxyl group and the other of $R^9$ and $R^{10}$ is

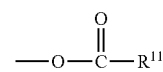

in which $R^{11}$ is an unsubstituted alkenyl group or an alkyl-substituted alkenyl group,
with the proviso that when X is a single bond, R is not a hydrogen atom.

Preferably, X is a single bond, $-(O-C_2H_4-)_n$, $-(O-C_3H_6-)_n$, or $-OC_3H_5(OH)-$.

Non-limiting examples of the alkyl group of $R^2$ and $R^3$ include methyl and ethyl. Nom-limiting examples of the alkenyl group of $R^2$ and $R^3$ include oxypropenyl and butenyl.

Non-limiting examples of the epoxy-containing group of R include an epoxy group and a glycidyl group. A non-limiting example of the alkenyl group of R is an allyl group. A non-limiting example of the unsaturated acyl group of R is an acryloyl group. A non-limiting example of the alkyl-substituted unsaturated acyl group of R is a methacryloyl group.

A non-limiting example of $R^4$ is an ethylene group.

Non-limiting examples of the alkyl group of $R^6$ and $R^7$ include methyl and ethyl.

Non-limiting examples of $R^{11}$ include a vinyl group and methylvinyl group.

A method for making a fluorene-containing compound according to the disclosure includes steps (a) to (c).

In step (a), a precursor compound having a formula (II) is provided:

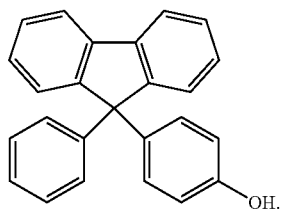

(II)

In step (b), a first organic compound is provided. The first organic compound is selected from the group consisting of alkenyl halide, alkylene oxide, an epoxy-containing unsaturated compound, an epoxy-containing alkyl halide, an unsaturated acyl halide, an alkyl-substituted unsaturated acyl halide, an unsaturated carboxylic acid, an alkyl-substituted unsaturated carboxylic acid, halohydrin,

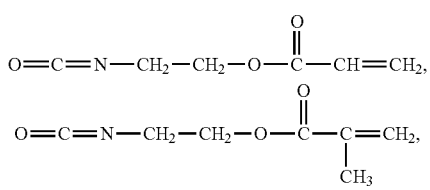

$O\!=\!C\!=\!N\!-\!R^4\!-\!R^5$, in which $R^4$ is an alkylene group and $R^5$ is an acrylate group or a methacrylate group, and combinations thereof.

In examples of the first organic compound, non-limiting examples of the alkenyl halide include allyl bromide and allyl chloride; non-limiting examples of the alkylene oxide include ethylene oxide, tetrahydrofuran, 1,2-epoxybutane, and propylene oxide; non-limiting examples of the epoxy-containing unsaturated compound include glycidyl acrylate, glycidyl methacrylate, and butenyl oxirane; a non-limiting example of the epoxy-containing alkyl halide is epichlorohydrin; non-limiting examples of the unsaturated acyl halide include acryloyl bromide and acryloyl chloride; non-limiting examples of the alkyl-substituted unsaturated acyl halide include methacryloyl bromide and methacryloyl chloride; a non-limiting example of the unsaturated carboxylic acid is acrylic acid; a non-limiting example of the alkyl-substituted unsaturated carboxylic acid is methacrylic acid; and non-limiting examples of the halohydrin include 3-chloro-1-propanol, 2-chloroethanol, and 2-bromoethanol.

In step (c), the precursor compound is reacted with the first organic compound in a first solvent to obtain a fluorene-containing compound of formula (III)

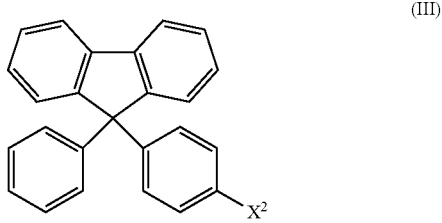

(III)

where $X^2$ is $-\!(\!O\!-\!X^1\!)_n\!OH$, or $-\!O\!-\!R^1$, in which n and $X^1$ are as defined above, and $R^1$ is selected from the group consisting of an alkenyl group, an epoxy-containing group, an unsaturated acyl group, an alkyl-substituted unsaturated acyl group,

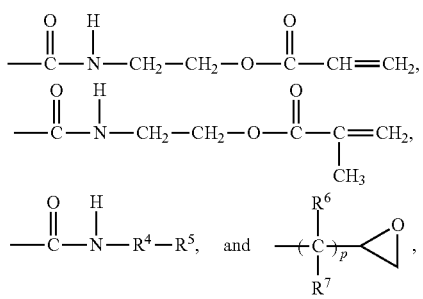

in which p, $R^6$, and $R^7$ are as defined above.

In examples of $R^1$, non-limiting examples of the alkenyl group, the epoxy-containing group, the unsaturated acyl group, and the alkyl-substituted unsaturated acyl group are the same as those of R.

The first solvent is selected from the group consisting of water, ether, ester, alcohol, halogenated hydrocarbon, hydrocarbon, alkyl substituted aromatic compound, ether alcohol ester, ether alcohol, ether ester, and combinations thereof.

In examples of the first solvent, non-limiting examples of the ether include 1,4-dioxane and tetrahydrofuran (THF); a non-limiting example of the ester is ethyl acetate; a non-limiting example of the alcohol is isopropanol (IPA); non-limiting example of the halogenated hydrocarbon include dichloromethane, chloroform, and chlorobenzene; a non-limiting example of the hydrocarbon is naphthenic oil; a non-limiting example of the alkyl substituted aromatic compound is toluene; a non-limiting example of the ether alcohol ester is diethylene glycol monoacetate (DGAc); a non-limiting example of the ether alcohol is ethylene glycol monobutyl ether (BCS); and a non-limiting example of the ether ester is ethylene glycol monoethyl ether acetate (CAC).

In one embodiment, the first organic compound is halohydrin or alkylene oxide, and the fluorene-containing compound has a formula (IV)

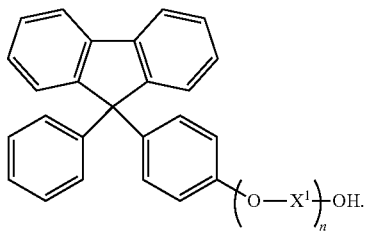

(IV)

In said one embodiment, the method may further include steps (d) and (e).

In step (d), a second organic compound is provided. The second organic compound is selected from the group consisting of alkenyl halide, an epoxy-containing unsaturated compound, an unsaturated acyl halide, an alkyl-substituted unsaturated acyl halide, an unsaturated carboxylic acid, an alkyl-substituted unsaturated carboxylic acid,

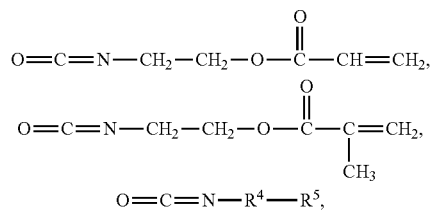

and combinations thereof. $R^4$ and $R^5$ are as defined above.

In examples of the second organic compound, non-limiting examples of the alkenyl halide, the epoxy-containing unsaturated compound, the unsaturated acyl halide, the alkyl-substituted unsaturated acyl halide, the unsaturated carboxylic acid, and the alkyl-substituted unsaturated carboxylic acid are the same as those of the first organic compound.

In step (e), the fluorene-containing compound of the formula (IV) is reacted with the second organic compound in a second solvent to obtain a fluorene-containing compound of formula (V)

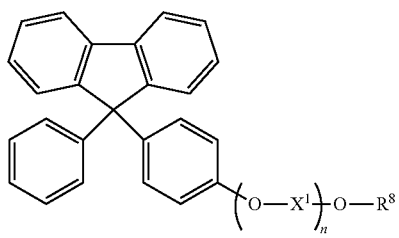

(V)

where $R^8$ is an alkenyl group, an unsaturated acyl group, an alkyl-substituted unsaturated acyl group,

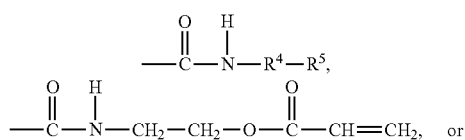

or

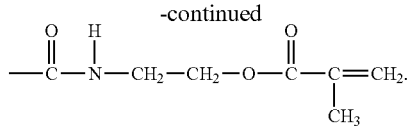

-continued

Non-limiting examples of the alkenyl group, the unsaturated acyl group, and the alkyl-substituted unsaturated acyl group of $R^8$ are the same as those of R.

In another embodiment, the first organic compound is an epoxy-containing alkyl halide, and the fluorene-containing compound has a formula (VI)

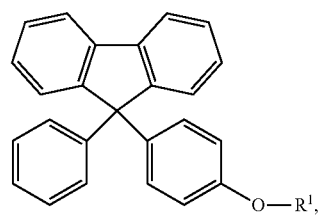

(VI)

where $R^1$ is

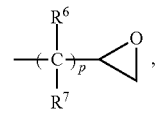

in which p, $R^6$, and $R^7$ are as defined above.

In said another embodiment, the method may further include steps (f) and (g).

In step (f), a third organic compound is provided. The third organic compound is selected form the group consisting of an unsaturated carboxylic acid, an alkyl-substituted unsaturated carboxylic acid, and combinations thereof. Non-limiting examples of the unsaturated carboxylic acid and the alkyl-substituted unsaturated carboxylic acid are the same as those of the first organic compound.

In step (g), the fluorene-containing compound of formula (VI) is reacted with the third organic compound in a third solvent to obtain a fluorene-containing compound of formula (VII)

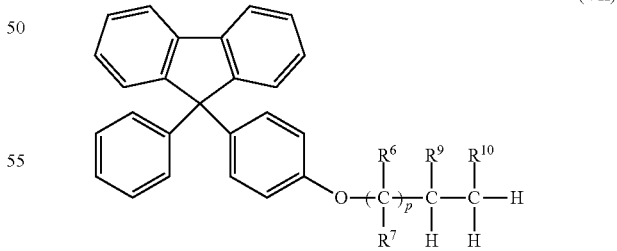

(VII)

where p, $R^6$, $R^7$, $R^9$, and $R^{10}$ are as defined above.

A curable composition according to an embodiment of the disclosure includes the fluorene-containing compound of formula (I) and an initiator. The initiator may be a photoinitiator or a thermal initiator. A non-limiting example of the photoinitiator is 1-hydroxycyclohexyl phenyl ketone. A non-limiting example of the thermal initiator is 2,2'-azobis(2-methylpropionitrile) (AIBN). The curable composition may further include a curable monomer. A non-limiting example of the curable monomer is 2-phenoxyethyl acrylate (PhEA).

A cured object made from the curable composition may be applied in an optical product, such as eyeglasses, lens, optical films (such as brightness enhancement films, reflective films, anti-reflection coatings, and so on), optical adhesives, etc. The cured object may be formed into the optical product using an injection molding machine, an extruder, an extrusion injection molding machine, a reaction injection molding machine, a coating machine, or a dispenser.

The embodiments of the disclosure will now be explained in more detail below by way of the following examples and comparative examples.

Synthesis Example 9-phenyl-9-fluorenol (10.32 g, 0.04 mole), acetic acid (360 g), and phenol (37.6 g, 0.4 mole) were stirred and mixed to obtain a yellow clear solution. 60 g of sulfuric acid was dropped into the yellow clear solution to obtain a red brown clear solution, and the red brown clear solution was stirred at room temperature for three days, followed by neutralization using a sodium hydroxide aqueous solution (50 wt %) and by filtration to obtain a filter cake. The filter cake was washed with plenty of hot water. Thereafter, the filter cake was solved in ethanol (50 wt %), and then was subjected to recrystallization, followed by filtration to obtain a white acicular powder. The white acicular powder was dried in a vacuum oven to obtain a product (11.6222 g, 86.9% yield).

The spectrum analysis for the product is: $^1$H-NMR (500 MHz, CDCl$_3$, 298K), δ(ppm): 7.81 (d, J=7.5 Hz, 2H), 7.451 (d, J=7.5 Hz, 2H), 7.413 (t, J=7.5 Hz, 2H), 7.324 (t, J=5.5 Hz, 2H), 7.24~7.73 (m, 5H), 7.13 (d, J=7 Hz, 2H), 6.739 (d, J=7 Hz, 2H), 4.915 (s, 1H, OH). The product was confirmed to have a chemical structure represented by

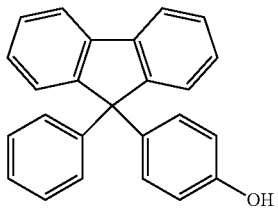 [SMILES: Oc1ccc(C2(c3ccccc3)c3ccccc3-c3ccccc32)cc1]

(hereinafter referred to as 4Ar-Phenol).

Example 1

4Ar-Phenol (3.34 g, 0.01 mole) obtained in the synthesis example, 1,4-dioxane (15 g), a sodium hydroxide aqueous solution (including 0.8 g of sodium hydroxide and 10 g of water), and isopropanol (10 g) were stirred, mixed, heated and kept at 40° C. for 1 hour to obtain a clear solution. Allyl bromide (14.5176 g, 0.12 mole) was dropped into the clear solution and the temperature was kept between 40° C. to 50° to obtain a light yellow clear solution. Thereafter, the light yellow clear solution was kept at 60° C. for reaction, and a thin-layer chromatography was used to monitor the progress of the reaction. The reaction was terminated after 48 hours to obtain a reaction product. Next, the reaction product was cooled to room temperature, washed with 70 g of water, followed by removal of water, and then subjected to condensation under a reduced pressure for removal of 1,4-dioxane to thereby obtain a clear viscose. Dichloromethane (10 g) and n-hexane (10 ml) were mixed with the clear viscose, and the temperature was reduced to and kept at −20° C. for 6 hours, followed by filtration to obtain a clear filtrate. The clear filtrate was subjected to condensation under a reduced pressure to obtain white crystals (2.8798 g, 77% yield).

The spectrum analysis for the white crystals is: $^1$H-NMR (500 MHz, CDCl$_3$, 298K), δ(ppm): 7.752 (d, J=7.5 Hz, 2H), 7.399 (d, J=7.5 Hz, 2H), 7.344 (t, J=7.5 Hz, 2H), 7.257 (t, J=7.5 Hz, 2H), 7.08~7.12 (m, 5H), 7.102 (d, J=9 Hz, 2H), 6.761 (d, J=9 Hz, 2H), 5.851~6.071 (m, 1H), 5.371 (dd, J=17 Hz, 1H), 5.271 (dd, J=12 Hz, 1H), 4.466 (d, J=5.5 Hz, 2H). The white crystals were confirmed to have a chemical structure represented by

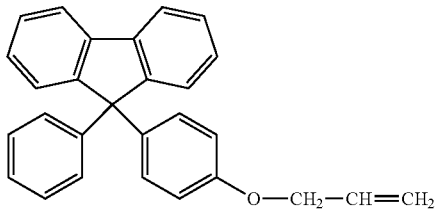 [SMILES: C=CCOc1ccc(C2(c3ccccc3)c3ccccc3-c3ccccc32)cc1]

(hereinafter referred to as 4Ar-Allyl).

Example 2

4Ar-Phenol (3.34 g, 0.01 mole) obtained in the synthesis example, triethylamine (1.5178 g, 0.015 mole), and anhydrous tetrahydrofuran (6 ml) were mixed and stirred under vacuum at −20° C. for 30 minutes to obtain a first clear solution. Acryloyl chloride (1.8102 g, 0.02 mole) was dropped into the first clear solution within 30 minutes, and the mixture was kept in reaction for 3 hours, to obtain a light yellow clear solution. Thereafter, 20 ml of water was added to the light yellow clear solution for extraction, followed by removal of water, to thereby obtain a second clear solution. Next, for removal of tetrahydrofuran, the second clear solution was subjected to condensation under a reduced pressure to obtain a white powder. The white powder was dissolved and purified using liquid chromatography. A wash liquid for the liquid chromatography included n-hexane and ethyl acetate (volume ratio of n-hexane to ethyl acetate=5:1), and the flow rate was set to 2 ml/min. The wash liquid was collected and subjected to condensation under a reduced pressure to obtain white crystals (2.328 g, 60% yield).

The spectrum analysis for the white crystals is: $^1$H-NMR (500 MHz, CDCl$_3$, 298K), δ(ppm): 7.694 (d, J=7.5 Hz, 2H), 7.324 (d, J=7.5 Hz, 2H), 7.291 (t, J=7.5 Hz, 2H), 7.199 (t, J=7.5 Hz, 2H), 7.105~7.18 (m, 7H), 6.911 (d, J=8.5 Hz, 2H), 6.496 (d, J=17.25 Hz, 1H), 6.180~6.245 (q, J=17 Hz, 1H), 5.911 (d, J=10.5 Hz, 1H). The white crystals were confirmed to have a chemical structure represented by

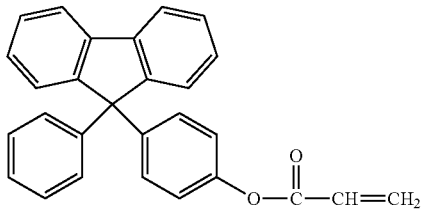 [SMILES: C=CC(=O)Oc1ccc(C2(c3ccccc3)c3ccccc3-c3ccccc32)cc1]

(hereinafter referred to as 4Ar-Acrylate).

Example 3

4Ar-Phenol (3.34 g, 0.01 mole) obtained in the synthesis example and ethyl acetate (7 ml) were mixed and stirred until dissolved, and then heated under reflux at 70° C. for 30 minutes to obtain a clear solution. Isocyanatoethyl methacrylate (2.02 g) was dropped into the clear solution for reaction for 3 hours to obtain a light yellow clear solution. Dibutyltin dilaurate (0.1 ml) was added to the light yellow clear solution for reaction for 2 hours, followed by cooling, and then addition of n-hexane (28 ml) to obtain a white cloudy solution. The white cloudy solution was subjected to recrystallization at −20° C. for 6 hours, followed by filtration to collect a filter cake. The filter cake was washed with ice n-hexane to obtain white acicular powder (4.3618 g, 89.2% yield).

The spectrum analysis for the white acicular powder is: $^1$H-NMR (500 MHz, CDCl$_3$, 298K), δ(ppm): 7.757 (d, J=7.5 Hz, 2H), 7.382 (d, J=7.5 Hz, 2H), 7.355 (t, J=7.5 Hz, 2H), 7.26 (t, J=8 Hz, 2H), 7.12~7.225 (m, 5H), 7.174 (d, J=9 Hz, 2H), 6.965 (d, J=8.5 Hz, 2H), 6.139 (d, 1H), 5.607 (d, 1H), 5.254 (s, 1H, NH), 4.288 (t, J=5.5 Hz, 2H), 3.571 (t, J=5.5 Hz, 2H), 1.956 (s, 1H). The white acicular powder was confirmed to have a chemical structure represented by

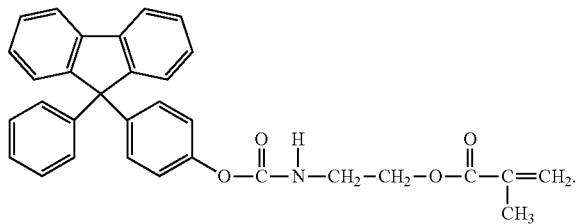 [SMILES: C=C(C)C(=O)OCCNC(=O)Oc1ccc(C2(c3ccccc3)c3ccccc3-c3ccccc32)cc1]

(hereinafter referred to as 4Ar-MOI).

Example 4

4Ar-Phenol (3.34 g, 0.01 mole) obtained in the synthesis example and ethyl acetate (7 ml) were mixed and stirred until dissolved, and then heated under reflux at 70° C. for 30 minutes to obtain a clear solution. Isocyanatoethyl acrylate (1.84 g) was dropped into the clear solution, and kept in reaction for 3 hours to obtain a light yellow clear solution. Dibutyltin dilaurate (0.1 ml) was added to the light yellow clear solution, and kept in reaction for 2 hours, followed by cooling, and by addition of n-hexane (28 ml) to obtain a white cloudy solution. The white cloudy solution was subjected to recrystallization at −20° C. for 6 hours, followed by filtration to collect a filter cake. The filter cake was washed with ice n-hexane to obtain white acicular powder (4.3755 g, 92% yield).

The spectrum analysis for the white acicular powder is: $^1$H-NMR (500 MHz, CDCl$_3$, 298K), δ(ppm): 7.757 (d, J=7.5 Hz, 2H), 7.382 (d, J=7.5 Hz, 2H), 7.355 (t, J=7.5 Hz, 2H), 7.263 (t, J=8 Hz, 2H), 7.12~7.24 (m, 7H), 7.174 (d, J=8.5 Hz, 2H), 6.967 (d, J=9 Hz, 2H), 6.432 (dd, J=17.5 Hz, 1H), 6.084~6.168 (q, J=17.25 Hz, 1H), 5.865 (dd, J=10.5 Hz, 1H), 5.3 (s, 1H, NH), 4.249 (t, J=5.5 Hz, 2H), 3.477~3.503 (q, J=11 Hz, 2H). The white acicular powder was confirmed to have a chemical structure represented by

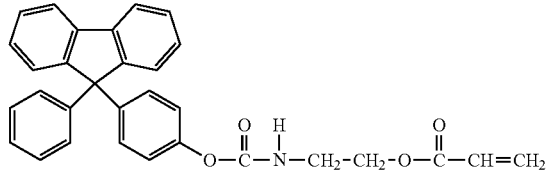 [SMILES: C=CC(=O)OCCNC(=O)Oc1ccc(C2(c3ccccc3)c3ccccc3-c3ccccc32)cc1]

(hereinafter referred to as 4Ar-AOI).

Example 5

4Ar-Phenol (3.34 g, 0.01 mole) obtained in the synthesis example, 2-chloroethanol (8.05 g, 0.1 mole), and isopropanol (10 ml) were stirred and mixed, and were heated to and kept at 40° C. until dissolved, to obtain a clear solution. A sodium hydroxide aqueous solution (including 0.4 g of sodium hydroxide and 4.6 g of water) was added into the clear solution, and heated to and kept at 65° C. for 6 hours for reaction, followed by cooling to room temperature. Thereafter, for removal of isopropanol, the reaction product was subjected to condensation under a reduced pressure to obtain a white crystal powder. The white crystal powder and dichloromethane (20 g) was mixed and then subjected to filtration to collect a clear filtrate. Next, 50 ml of n-hexane was added to the clear filtrate and then kept at −20° C. for 6 hours, followed by filtration to collect a white powder (3.3455 g, 88.5% yield).

The spectrum analysis for the white powder is: $^1$H-NMR (500 MHz, CDCl$_3$, 298K), δ(ppm): 7.755 (d, J=7.5 Hz, 2H), 7.386 (d, J=7.5 Hz, 2H), 7.364 (t, J=7.5 Hz, 2H), 7.262 (t, J=7.5 Hz, 2H), 7.16~7.24 (m, 5H), 7.118 (d, J=9 Hz, 2H), 6.768 (d, J=9 Hz, 2H), 4.020 (t, J=4.5 Hz, 2H), 3.914 (t, J=4.5 Hz, 2H), 1.974 (s, 1H, OH). The white powder was confirmed to have a chemical structure represented by

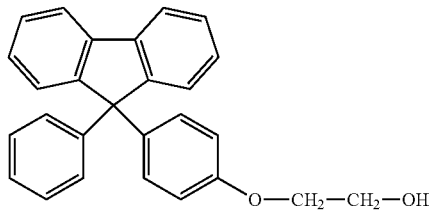 [SMILES: OCCOc1ccc(C2(c3ccccc3)c3ccccc3-c3ccccc32)cc1]

(hereinafter referred to as 4Ar-EtOH).

Example 6

4Ar-EtOH (1.134 g, 0.003 mole) obtained in Example 5, toluene (10 g), acrylic acid (0.864 g, 0.012 mole), methanesulfonic acid (0.24 g), and hydroquinone monomethyl ether (0.04 g) were stirred, mixed, and heated to and kept at 70° C. for 1 hour until dissolved to obtain a first clear solution. For reaction, the first clear solution was heated to and kept at 90° C. for 1 hour, at 105° C. for 1 hour, and at 110° C. for 1 hour, followed by cooling to room temperature to obtain a reaction product. A sodium hydroxide aqueous solution (including 0.1 g of sodium hydroxide and 20 g of water) was added to the reaction product for extraction, followed by removal of the aqueous solution to obtain a second clear solution. For extraction, water was added to the second clear solution, followed by removal of the water. Such extraction step was repeated for twice, followed by condensation under a reduced pressure for removal of toluene to obtain a third clear solution. The third clear solution was purified using liquid chromatography. A wash liquid for the liquid chromatography included n-hexane and ethyl acetate (volume ratio of n-hexane to ethyl acetate=5:1), and the flow rate was set to 4 ml/min. The wash liquid was collected and subjected to condensation under a reduced pressure to obtain a clear liquid (0.9007 g, 69.5% yield).

The spectrum analysis for the clear liquid is: $^1$H-NMR (500 MHz, CDCl$_3$, 298K), δ(ppm): 7.76 (d, J=7.5 Hz, 2H), 7.387 (d, J=7.5 Hz, 2H), 7.366 (t, J=7.5 Hz, 2H), 7.273 (t, J=7.5 Hz, 2H), 7.12~7.20 (m, 5H), 7.117 (d, J=9 Hz, 2H), 6.771 (d, J=9 Hz, 2H), 6.433 (d, J=17 Hz, 1H), 5.963~6.132 (q, J=17 Hz, 1H), 5.811 (d, J=9 Hz, 1H), 4.572 (t, J=4.5 Hz, 2H), 4.222 (t, J=4.5 Hz, 2H). The clear liquid was confirmed to have a chemical structure represented by

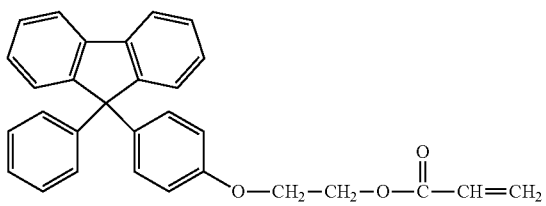 [SMILES: C=CC(=O)OCCOc1ccc(C2(c3ccccc3)c3ccccc3-c3ccccc32)cc1]

(hereinafter referred to as 4Ar-Et-Acrylate).

Example 7

4Ar-EtOH (1.134 g, 0.003 mole) obtained in Example 5, 1,4-dioxane (8 g), a sodium hydroxide aqueous solution (including 0.12 g of sodium hydroxide and 5 g of water), and isopropanol (8 g) were stirred, mixed, heated and kept at 40° C. for 0.5 hour to obtain a clear solution. Allyl bromide (2.177 g, 0.018 mole) was dropped into the clear solution and the temperature was kept between 40° C. to 50° C., to obtain a light yellow clear solution. Thereafter, the light yellow clear solution was kept at 70° C. for reaction, and a thin-layer chromatography was used to monitor the progress of the reaction. The reaction was terminated after 48 hours to obtain a reaction product. Next, the reaction product was cooled to room temperature, washed with water followed by removal of water, and then subjected to condensation under a reduced pressure for removal of 1,4-dioxane to thereby obtain a yellow clear viscose. Dichloromethane (10 g) and n-hexane (5 ml) were mixed with the yellow clear viscose, and the temperature was reduced to and kept at −20° C. for 6 hours, followed by filtration to obtain a clear filtrate. The clear filtrate was subjected to condensation under a reduced pressure to obtain light yellow crystals (0.6988 g, 87.6% yield).

The spectrum analysis for the light yellow crystals is: $^1$H-NMR (500 MHz, CDCl$_3$, 298K), δ(ppm): 7.766 (d, J=7.5 Hz, 2H), 7.387 (d, J=7.5 Hz, 2H), 7.366 (t, J=7.5 Hz, 2H), 7.273 (t, J=7.5 Hz, 2H), 7.08~7.14 (m, 5H), 7.107 (d, J=9 Hz, 2H), 6.777 (d, J=9 Hz, 2H), 5.9~6.14 (m, 1H), 5.241 (d, 1H), 5.232 (d, J=5.5 Hz, 1H), 4.122 (t, J=4.5 Hz, 2H), 4.072 (d, J=6.0 Hz, 2H), 3.788 (t, J=4.5 Hz, 2H). The light yellow crystals were confirmed to have a chemical structure represented by

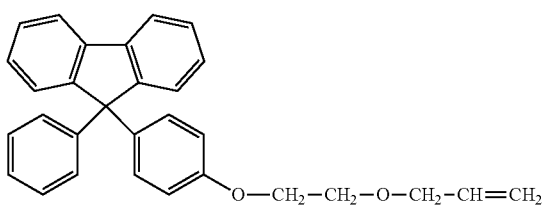 [SMILES: C=CCOCCOc1ccc(C2(c3ccccc3)c3ccccc3-c3ccccc32)cc1]

(hereinafter referred to as 4Ar-Et-Allyl).

Example 8

4Ar-EtOH (1.134 g, 0.003 mole) obtained in Example 5 and ethyl acetate (5 ml) were mixed and stirred until dissolved, and then heated under reflux at 75° C. for 30 minutes to obtain a clear solution. Isocyanatoethyl acrylate (1.270 g, 0.009 mole) was dropped into the clear solution for reaction for 8 hours to obtain a light yellow clear solution. A solution of dibutyltin dilaurate (0.1196 g, 5 wt %) was added to the light yellow clear solution for reaction for 5 hours, followed by cooling, and then addition of n-hexane (20 ml) to obtain a white cloudy solution. The white cloudy solution was subjected to recrystallization at −20° C. for 6 hours, followed by filtration to collect a filter cake. The filter cake was washed with ice n-hexane to obtain white acicular powder (1.3800 g, 88.6% yield).

The spectrum analysis for the white acicular powder is: $^1$H-NMR (500 MHz, CDCl$_3$, 298K), δ(ppm): 7.566 (d, J=7.5 Hz, 2H), 7.365 (d, J=7.5 Hz, 2H), 7.355 (t, J=7.5 Hz, 2H), 7.268 (t, J=7.5 Hz, 2H), 7.06~7.15 (m, 5H), 7.111 (d, J=9 Hz, 2H), 6.857 (d, J=9 Hz, 2H), 6.439 (d, J=17.5 Hz, 1H), 6.081~6.173 (d, 1H), 5.293 (s, 1H, NH), 5.8522 (d, J=17.25 Hz, 1H), 4.511 (t, J=4.5 Hz, 2H), 4.458 (t, J=4.5 Hz, 2H), 4.2429 (t, J=4.5 Hz, 2H), 3.166~3.202 (q, J=8 Hz, 2H). The white acicular powder was confirmed to have a chemical structure represented by

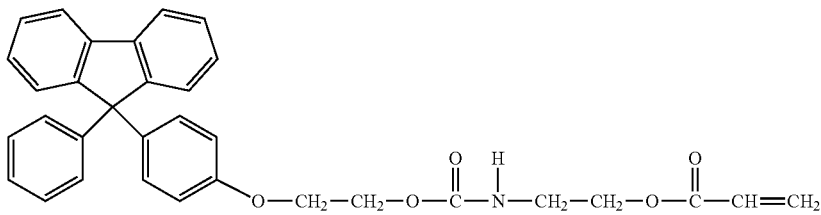 [SMILES: C=CC(=O)OCCNC(=O)OCCOc1ccc(C2(c3ccccc3)c3ccccc3-c3ccccc32)cc1]

(hereinafter referred to as 4Ar-Et-AOI).

Example 9

4Ar-EtOH (1.134 g, 0.003 mole) obtained in Example 5 and ethyl acetate (5 ml) were mixed and stirred until dissolved, and then heated under reflux at 75° C. for 30 minutes to obtain a clear solution. Isocyanatoethyl methacrylate (1.395 g, 0.009 mole) was dropped into the clear solution for reaction for 8 hours to obtain a light yellow clear solution. A solution of dibutyltin dilaurate (0.13 g, 5 wt %) was added to the light yellow clear solution for reaction for 5 hours, followed by cooling, and then addition of n-hexane (20 ml) to obtain a white cloudy solution. The white cloudy solution was subjected to recrystallization at −20° C. for 6 hours, followed by filtration to collect a filter cake. The filter cake was washed with ice n-hexane to obtain white acicular powder (1.366 g, 85.4% yield).

The spectrum analysis for the white acicular powder is: $^1$H-NMR (500 MHz, CDCl$_3$, 298K), δ(ppm): 7.666 (d, J=7.5 Hz, 2H), 7.455 (d, J=7.5 Hz, 2H), 7.367 (t, J=7.5 Hz, 2H), 7.299 (t, J=7.5 Hz, 2H), 7.10~7.18 (m, 5H), 7.134 (d, J=9 Hz, 2H), 6.677 (d, J=9 Hz, 2H), 6.123 (d, 1H), 5.7495 (d, 1H), 5.293 (s, 1H, NH), 4.578 (t, J=4.5 Hz, 2H), 4.424 (t, J=4.5 Hz, 2H), 4.2829 (t, J=4.5 Hz, 2H), 3.143~3.423 (q, J=8.2 Hz, 2H), 1.891 (s, 3H). The white acicular powder was confirmed to have a chemical structure represented by

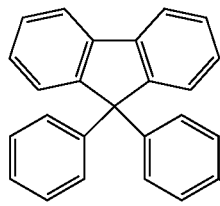
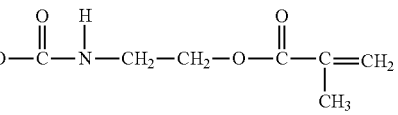

(hereinafter referred to as 4Ar-Et-MOI).

Example 10

4Ar-Phenol (3.34 g, 0.01 mole) obtained in the synthesis example, 1,4-dioxane (15 g), a sodium hydroxide aqueous solution (including 0.14 g of sodium hydroxide and 4.86 g of water), and isopropanol (10 g) were placed in a stainless steel high pressure reactor, and were stirred, mixed, heated and kept at 40° C. for 1 hour to obtain a clear solution. After the clear solution was cooled to room temperature, propylene oxide (0.78 g, 0.013 mole) was added to the clear solution, the temperature was kept at 60° C. for 24 hours for reaction, and a thin-layer chromatography was used to monitor the progress of the reaction. After the reaction was terminated, the reaction product was cooled to room temperature, washed with 70 g of water followed by removal of the water, and then subjected to condensation under a reduced pressure for removal of 1,4-dioxane to obtain a viscose. Dichloromethane (10 g) and n-hexane (10 ml) were mixed with the viscose, and the temperature was reduced to and kept at −20° C. for 6 hours, followed by filtration to obtain a clear filtrate. The clear filtrate was subjected to column chromatography for purification. A wash liquid for the column chromatography included dichloromethane and n-hexane. The wash liquid was collected and subjected to condensation under a reduced pressure to obtain a white powder (26% yield).

The spectrum analysis for the white powder is: $^1$H-NMR (500 MHz, CDCl$_3$, 298K), δ(ppm): 7.783 (d, 2H), 7.388 (d, 2H), 7.376 (t, 2H), 7.260 (t, 2H), 7.18~7.22 (m, 5H), 7.106 (d, 2H), 6.762 (d, 2H), 4.160 (m, 1H), 3.806~3.882 (d, 2H), 2.466 (m, 1H), 1.276 (m, 3H). The white powder was confirmed to have a chemical structure represented by

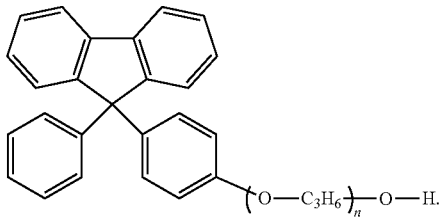

When calculated by 1H-NMR integration, n is about 1.32. The hydroxyl number determined by ASTM D4274-05 is 138.2 mgKOH/g, and thus n is calculated to be about 1.24. An average value of n is 1.3. The white powder obtained in Example 10 is hereinafter referred to as 4Ar-PG$_{1.3}$.

Example 11

4Ar-PG$_{1.3}$ (1.193 g, 0.003 mole) obtained in Example 10, toluene (10 g), acrylic acid (0.864 g, 0.012 mole), methanesulfonic acid (0.24 g), and hydroquinone monomethyl ether (0.04 g) were stirred, mixed, and heated to and kept at 70° C. for 1 hour until dissolved to obtain a first clear solution. For reaction, the first clear solution was heated to and kept at 90° C. for 1 hour, at 105° C. for 1 hour, and at 110° C. for 1 hour, followed by cooling to room temperature to obtain a reaction product. A sodium hydroxide aqueous solution (including 0.1 g of sodium hydroxide and 20 g of water) was added to the reaction product for extraction, followed by removal of the aqueous solution to obtain a second clear solution. For water extraction, water was added to the second clear solution, followed by removal of the water. The water extraction step was repeated for twice, followed by condensation under a reduced pressure for removal of toluene to obtain a third clear solution. The third clear solution was purified using liquid chromatography. A wash liquid for the liquid chromatography included n-hexane and ethyl acetate (volume ratio of n-hexane to ethyl acetate=5:1). The wash liquid was collected and subjected to condensation under a reduced pressure to obtain a clear liquid (0.762 g, 56.2% yield).

The spectrum analysis for the clear liquid is: $^1$H-NMR (300 MHz, CDCl$_3$, 298K), δ(ppm): 7.78 (d, 2H), 7.38 (d, 2H), 7.37 (t, 2H), 7.25 (t, 2H), 7.16~7.23 (m, 5H), 7.10 (d, 2H), 6.75 (d, 2H), 6.44 (m, 1H), 5.94~6.13 (m, 1H), 5.82 (m, 1H), 4.14~3.78 (series of multi-peaks), 1.28 (m). The clear liquid was confirmed to have a chemical structure represented by

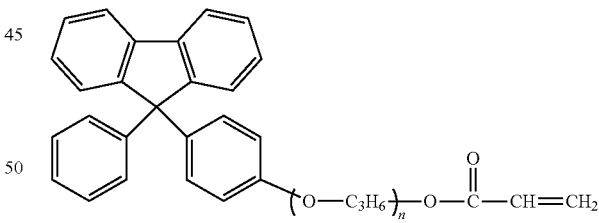

(hereinafter referred to as 4Ar-PG$_{1.3}$-Acrylate).

Example 12

4Ar-Phenol (3.34 g, 0.01 mole) obtained in the synthesis example, propylene glycol monomethyl ether acetate (15 g), tetrabutylphosphonium bromide (0.170 g), glycidyl methacrylate (1.78 g, 0.0125 mole), and di-tert-butyl-4-hydroxytoluene (BHT, 0.0045 g) were mixed and stirred in a four-neck flask to which dried air was introduced, and heated and kept at 105° C. 0.0045 g of di-tert-butyl-4-hydroxytoluene was further added every 2 hours, and a thin-layer chromatography was used to monitor the progress of the reaction. The reaction was terminated after 10 hours to obtain a reaction product. Next, the reaction product was cooled to room temperature, and then subjected to condensation under a reduced pressure for removal of solvents to obtain a condensed product. The condensed product was washed by addition of a mixture solution of dichloromethane (15 g) and an aqueous sodium bicarbonate solution (70 g, 5 wt %) for a while, followed by removal of the mixture solution. The wash step was repeated, followed by drying to obtain a viscose. Dichloromethane (10 g) and n-hexane (10 ml) were mixed with the viscose, and the temperature was reduced to and kept at −20° C. for 6 hours, followed by filtration to obtain a clear filtrate. The clear filtrate was purified using column chromatography. A wash liquid for the column chromatography included n-hexane and ethyl acetate (volume ratio of n-hexane to ethyl acetate=3:1). The wash liquid was collected and subjected to condensation under a reduced pressure to obtain a white powder (17% yield).

The spectrum analysis for the white powder is: $^1$H-NMR (500 MHz, CDCl$_3$, 298K), δ(ppm): 7.762 (d, 2H), 7.364 (t, 2H), 7.272 (t, 2H), 7.385 (d, 2H), 7.12~7.22 (m, 5H), 7.114 (d, 2H), 6.780 (d, 2H), 6.225 (m, 1H), 5.587 (s, 1H), 3.916~4.362 (b, 6H,

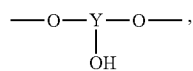

Y is C$_3$H$_5$), 1.908 (s, 3H). The white powder was confirmed to have a chemical structure represented by

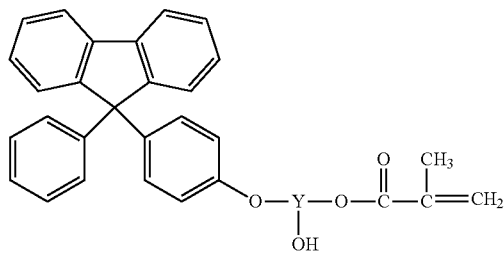

in which Y is C$_3$H$_5$, (hereinafter referred to as 4Ar-GMA).

Example 13

4Ar-Phenol (3.34 g, 0.01 mole) obtained in the synthesis example, 1,4-dioxane (15 g), tetraethyl ammonium bromide (TEAB, 0.21 g, 0.001 mole), and epichlorohydrin (4.7 ml, 0.06 mole) were mixed and stirred in a reaction flask, and heated and kept at 65° C. for 1 hour. Thereafter, a sodium hydroxide aqueous solution (1.2 ml, 50 wt %) was dropped into the reaction flask within 0.5 hour, and then kept in reaction for 2.5 hours to obtain a reaction product. After the reaction product was cooled, the reaction product was (1) filtered and vacuum dried for removal of excess epichlorohydrin, (2) dissolved in dichloromethane, (3) washed with 70 g of water, followed by removal of water, (4) subjected to vacuum-condensation, and (5) precipitated in an ethanol aqueous solution (volume ratio of ethanol to water=3:1). Thereafter, the reaction product was further filtered, dissolved, and precipitated for several times, followed by vacuum drying at 45° C. to obtain a product (63% yield).

The spectrum analysis for the product is: $^1$H-NMR (300 MHz, CDCl$_3$, 298K), δ(ppm): 7.76 (d, 2H), 7.39 (d, 2H), 7.37 (t, 2H), 7.26 (t, 2H), 7.13~7.22 (m, 5H), 7.12 (d, 2H), 6.78 (d, 2H), 4.52~3.93 (m, 2H), 3.46 (m, 1H), 2.86~2.73 (d, 2H). The product was confirmed to have a chemical structure represented by (hereinafter referred to as 4Ar-GE).

Example 14

4Ar-GE (3.9 g, 0.01 mole) obtained in Example 13, propylene glycol monomethyl ether acetate (15 g), benzyl triphenyl phosphonium chloride (BzTPPC, 0.0778 g, 0.0002 mole), acrylic acid (0.86 g, 0.012 mole), phenothiazine (PTZ, 0.0020 g, 0.00001 mole), and di-tert-butyl-4-hydroxytoluene (0.0044 g, 0.00002 mole) were mixed and stirred in a four-neck flask to which dried air was introduced, and heated and kept at 105° C. 0.0022 g of di-tert-butyl-4-hydroxytoluene was further added every 2 hours, and a thin-layer chromatography was used to monitor the progress of the reaction. The reaction was terminated after 12 hours to obtain a reaction product. Next, the reaction product was subjected to condensation under a reduced pressure for removal of solvents, followed by addition of 20 ml of dichloromethane to obtain a dichloromethane solution. The dichloromethane solution was washed with a hydrochloric acid aqueous solution (70 g, 0.1 vol/wt %), followed by removal of the hydrochloric acid aqueous solution, and then washed with a sodium bicarbonate aqueous solution (70 g, 5 wt %), followed by removal of the sodium bicarbonate aqueous solution. The wash step was repeated for several times, followed by vacuum drying to obtain a viscose. Dichloromethane (10 g) and n-hexane (10 ml) were mixed with the viscose, and the temperature was reduced to and kept at −20° C. for 6 hours, followed by filtration to obtain a clear filtrate. The clear filtrate was purified using column chromatography. A wash liquid for the column chromatography included ethyl acetate and hexane (volume ratio of ethyl acetate to hexane=1:3). The wash liquid was collected and subjected to condensation under a reduced pressure to obtain a product (58% yield).

The spectrum analysis for the product is: $^1$H-NMR (300 MHz, CDCl$_3$, 298K), δ(ppm): 7.75 (d, 2H), 7.37 (d, 2H), 7.36 (t, 2H), 7.24 (t, 2H), 7.12~7.24 (m, 5H), 7.10 (d, 2H), 6.80 (d, 2H), 6.34 (d, 1H), 6.08 (m, 1H), 5.87 (d, 1H), 3.94~4.38 (m, 5H, Y is C$_3$H$_5$), 2.53 (s, 1H). The product was confirmed to have a chemical structure represented by

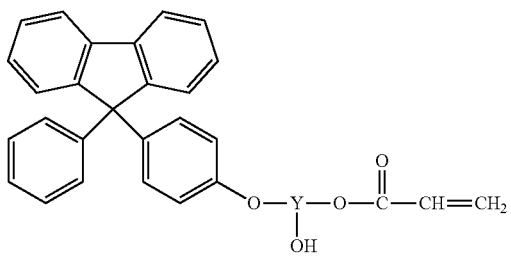

(hereinafter referred to as 4Ar-GE-AA).

Refractive Index

A refractive index of each of the samples obtained in synthesis example and Examples 1 to 14 was measured using a refractometer (ATAGO, DR-A1-Plus) based on the following steps. The sample was dissolved in ethyl acetate in different concentrations, and the refractive index of each of the different concentration solutions was measured at 25° C. five times, and an average value thereof was calculated. The average values of the refractive indexes of the different concentration solutions were plotted versus the concentrations of the different concentration solutions. The refractive index of the sample (i.e., the fluorene-containing compound) was extrapolated from the plot. The results are shown in Table 1.

TABLE 1

| Fluorene-containing compound | | Refractive index |
|---|---|---|
| Synthesis Example | 4Ar-Phenol | 1.740 |
| Example 1 | 4Ar-Allyl | 1.660 |
| Example 2 | 4Ar-Acrylate | 1.680 |
| Example 3 | 4Ar-MOI | 1.570 |
| Example 4 | 4Ar-AOI | 1.570 |
| Example 5 | 4Ar-EtOH | 1.650 |
| Example 6 | 4Ar-Et-Acrylate | 1.634 |
| Example 7 | 4Ar-Et-Allyl | 1.610 |
| Example 8 | 4Ar-Et-AOI | 1.550 |
| Example 9 | 4Ar-Et-MOI | 1.540 |
| Example 10 | 4Ar-PG$_{1.3}$ | 1.636 |
| Example 11 | 4Ar-PG$_{1.3}$-acrylate | 1.621 |
| Example 12 | 4Ar-GMA | 1.623 |
| Example 13 | 4Ar-GE | 1.643 |
| Example 14 | 4Ar-GE-AA | 1.624 |

It can be noted from the results shown in Table 1 that the fluorene-containing compounds of Examples 1 to 14 have a refractive index not less than 1.54.

Example 15

2-phenoxyethyl acrylate (91 wt %), 4Ar-Allyl obtained in Example 1 (5 wt %), and 1-hydroxycyclohexyl phenyl ketone (4 wt %, Ciba-Geigy, Irgacure® 184) were evenly mixed to obtain a curable composition. The curable composition was coated on a film of polyethylene terephthalate (PET film) using a coating knife to have a thickness of 0.26 mm. The curable composition was cured by irradiation of UV light (250 mJ/cm$^2$) for four times. Infrared spectrometer was used to check whether or not the curable composition was cured. When no more changes of the absorption peak (1620 cm$^{-1}$) of the C=C group was detected, a cured object was formed on the PET film.

Examples 16 to 26

Cured objects of Examples 16 to 26 were each prepared according to a procedure similar to that described in Example 15. In Examples 16 to 26, 4Ar-Allyl of Example 1 was replaced by 4Ar-Acrylate of Example 2, 4Ar-MOI of Example 3, 4Ar-AOI of Example 4, 4Ar-EtOH of Example 5, 4Ar-Et-Acrylate of Example 6, 4Ar-Et-Allyl of Example 7, 4Ar-Et-AOI of Example 8, 4Ar-Et-MOI of Example 9, 4Ar-PG$_{1.3}$ of Example 10, 4Ar-PG$_{1.3}$-acrylate of Example 11, and 4Ar-GMA of Example 12, respectively.

Example 27

4Ar-AOI obtained in Example 4 (1 g) was dissolved in tetrahydrofuran (5 g), 0.004 g of 2,2'-azobis(2-methylpropionitrile) was then added, and heated to and kept at 65° C. for reaction for 5 hours. After the reaction was terminated, 20 g of methanol was added to precipitate a product. The product was subjected to filtration to collect a filter cake, followed by drying to obtain a white powder (0.87 g).

Comparative Example 2-phenoxyethyl acrylate (96 wt %) and 1-hydroxycyclohexyl phenyl ketone (4 wt %, Ciba-Geigy, Irgacure® 184) were evenly mixed to obtain a curable composition. The curable composition was coated on a PET film using a coating knife to have a thickness of 0.26 mm. The curable composition was cured by irradiation of UV light (250 mJ/cm$^2$) for four times. Infrared spectrometer was used to check whether or not the curable composition was cured. When no more changes of the absorption peak (1620 cm$^{-1}$) of the C=C group was detected, a cured object was formed on the PET film.

Molecular Weight

The white powder obtained in Example 27 (0.1 g) was dissolved in 1-methyl-2-pyrrolidone (NMP, 10 g), followed by filtration using a filter with a pore size of 0.45 microns to collect a filtrate. 15 μl of the filtrate was applied to GPC (gel permeation chromatography, Elite LaChrom, Hitachi L-2130) using NMP as an eluting solvent (flow rate=0.5 ml/min). The detector employed to measure the molecular weights of the white powder in NMP at 35° C. was a RI detector. The average molecular weight of the white powder was 26600.

Yellowing Test

CIE b* color values of the cured products of Examples 15 to 18 and 20 to 23 and Comparative Example were measured using a UV-Vis infrared spectrometer (V-670, JASCO Corporation), and then placed in an oven at a temperature 130° C. The CIE b* color values of the cured products were further measured after placed in the oven for 12 hours, 24, hours, 36 hours, 48 hours, and 60 hours, respectively. The results are listed in Table 2.

TABLE 2

| | $b_{0\,hr}$ | $\Delta b^* = b_{t,\,hr} - b_{0\,hr}$ | | | | |
|---|---|---|---|---|---|---|
| | | Hours | | | | |
| | 0 | 12 | 24 | 26 | 48 | 60 |
| Example 15 | −0.14 | 0.25 | 0.31 | 0.31 | 0.54 | 0.77 |
| Example 16 | −0.19 | 0.25 | 0.31 | 0.31 | 0.53 | 0.72 |
| Example 17 | −0.03 | 0.24 | 0.25 | 0.25 | 0.42 | 0.68 |
| Example 18 | −0.04 | 0.25 | 0.25 | 0.27 | 0.44 | 0.62 |
| Example 20 | −0.18 | 0.25 | 0.28 | 0.29 | 0.54 | 0.77 |
| Example 21 | −0.15 | 0.23 | 0.33 | 0.33 | 0.54 | 0.78 |
| Example 22 | −0.04 | 0.25 | 0.27 | 0.27 | 0.43 | 0.66 |
| Example 23 | −0.04 | 0.25 | 0.25 | 0.28 | 0.44 | 0.67 |
| Comparative Example | −0.19 | 0.25 | 0.37 | 0.37 | 0.62 | 0.92 |

It can be noted from the results shown in Table 2 that the cured product of Comparative Example has larger differential values (Δb*) than those of Examples 15 to and 20 to 23. Therefore, the cured products of Examples 15 to 18 and 20 to 23 are less likely to turn yellowing after using for a time period.

Light Transmittance Test

The cured products of Examples 15 to 18 and 20 to 23 and Comparative Example, and a PET film were subjected to a light transmittance test using a UV-Vis infrared spectrometer. The results are list in Table 3.

TABLE 3

|  | Transmittance (%) | | |
|---|---|---|---|
|  | Blue (470 nm) | Yellow (570 nm) | Red (660 nm) |
| Example 15 | 88.6 | 89.6 | 89.8 |
| Example 16 | 89.2 | 89.3 | 89.6 |
| Example 17 | 89.5 | 89.5 | 89.5 |
| Example 18 | 89.5 | 89.5 | 89.5 |
| Example 20 | 89.1 | 89.3 | 89.5 |
| Example 21 | 88.5 | 89.6 | 89.7 |
| Example 22 | 89.4 | 89.4 | 89.4 |
| Example 23 | 89.4 | 89.4 | 89.5 |
| Comparative Example | 88.4 | 88.7 | 89.1 |
| PET film | 88.3 | 88.3 | 88.3 |

It can be noted from the results shown in Table 3 that all of the cured products of Examples have better/higher light transmittance in the blue, yellow, and red regions of the spectrum.

While the present disclosure has been described in connection with what are considered the most practical and preferred embodiments, it is understood that this invention is not limited to the disclosed embodiments but is intended to cover various arrangements included within the spirit and scope of the broadest interpretations and equivalent arrangements.

What is claimed is:

1. A fluorene-containing compound having a formula (I)

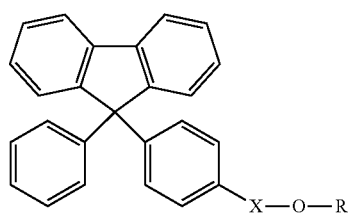

(I)

where:
X is a single bond or —OC$_3$H$_5$(OH)—; and
R is selected from the group consisting of a hydrogen atom, an epoxy-containing group, an alkenyl group, an unsaturated acyl group, an alkyl-substituted unsaturated acyl group,

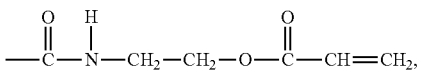

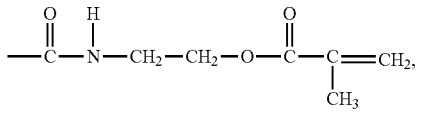

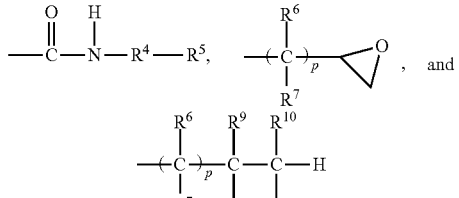

in which

R$^4$ is an alkylene group,

R$^5$ is an acrylate group or a methacrylate group, p ranges from 1 to 4, each of R$^6$ and R$^7$ is the same or different in each repeating unit p, and is independently a hydrogen atom, an alkyl group, or a hydroxyl group, and one of R$^9$ and R$^{10}$ is a hydroxyl group and the other of R$^9$ and R$^{10}$ is

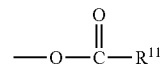

in which R$^{11}$ is an unsubstituted alkenyl group or an alkyl-substituted alkenyl group, with the proviso that when X is a single bond, R is not a hydrogen atom.

2. The fluorene-containing compound according to claim 1, wherein X is a single bond, and R is an unsaturated acyl group.

3. The fluorene-containing compound according to claim 1, wherein X is —OC$_3$H$_5$(OH)—, and R is an unsaturated acyl group.

4. A curable composition comprising a fluorene-containing compound as claimed in claim 1.

5. The curable composition according to claim 4, further comprising an initiator.

6. A polymer composition comprising a curable composition as claimed in claim 4.

* * * * *